United States Patent [19]

Bonnet

[11] 4,024,869

[45] May 24, 1977

[54] RESECTOSCOPES

[75] Inventor: Ludwig Bonnet, Knittligen, Germany

[73] Assignee: Richard Wolf GmbH, Knittlingen, Germany

[22] Filed: Dec. 8, 1975

[21] Appl. No.: 638,424

[30] Foreign Application Priority Data

Dec. 20, 1974 Germany ............... 7442379[U]

[52] U.S. Cl. .......................... 128/303.15
[51] Int. Cl.² ............................ A61B 17/32
[58] Field of Search ........... 128/303.15, 303.13, 128/303.14, 303.16, 303.17

[56] References Cited

UNITED STATES PATENTS

| 1,952,617 | 3/1934 | Wappler | 128/303.15 |
| 2,011,169 | 8/1935 | Wappler | 128/303.15 |
| 2,032,860 | 3/1936 | Wappler et al. | 128/303.15 |

FOREIGN PATENTS OR APPLICATIONS

| 321,112 | 12/1902 | France | 128/303.14 |
| 727,837 | 10/1942 | Germany | 128/303.15 |

*Primary Examiner*—Robert W. Michell
*Assistant Examiner*—Lee S. Cohen
*Attorney, Agent, or Firm*—Kinzer, Plyer, Dorn & McEachran

[57] ABSTRACT

A resectoscope has an outer barrel and an inner tube which have, at a distal end region of the resectoscope, respective angled portions which constitute the jaws of a forceps having, at a proximal end region of the resectoscope, a scissors grip comprising two limbs which are connected to the barrel and the inner tube respectively, the inner tube being adapted to receive an optical system to be passed therethrough, and an insulated cutting loop being carried by one of the jaws.

7 Claims, 5 Drawing Figures

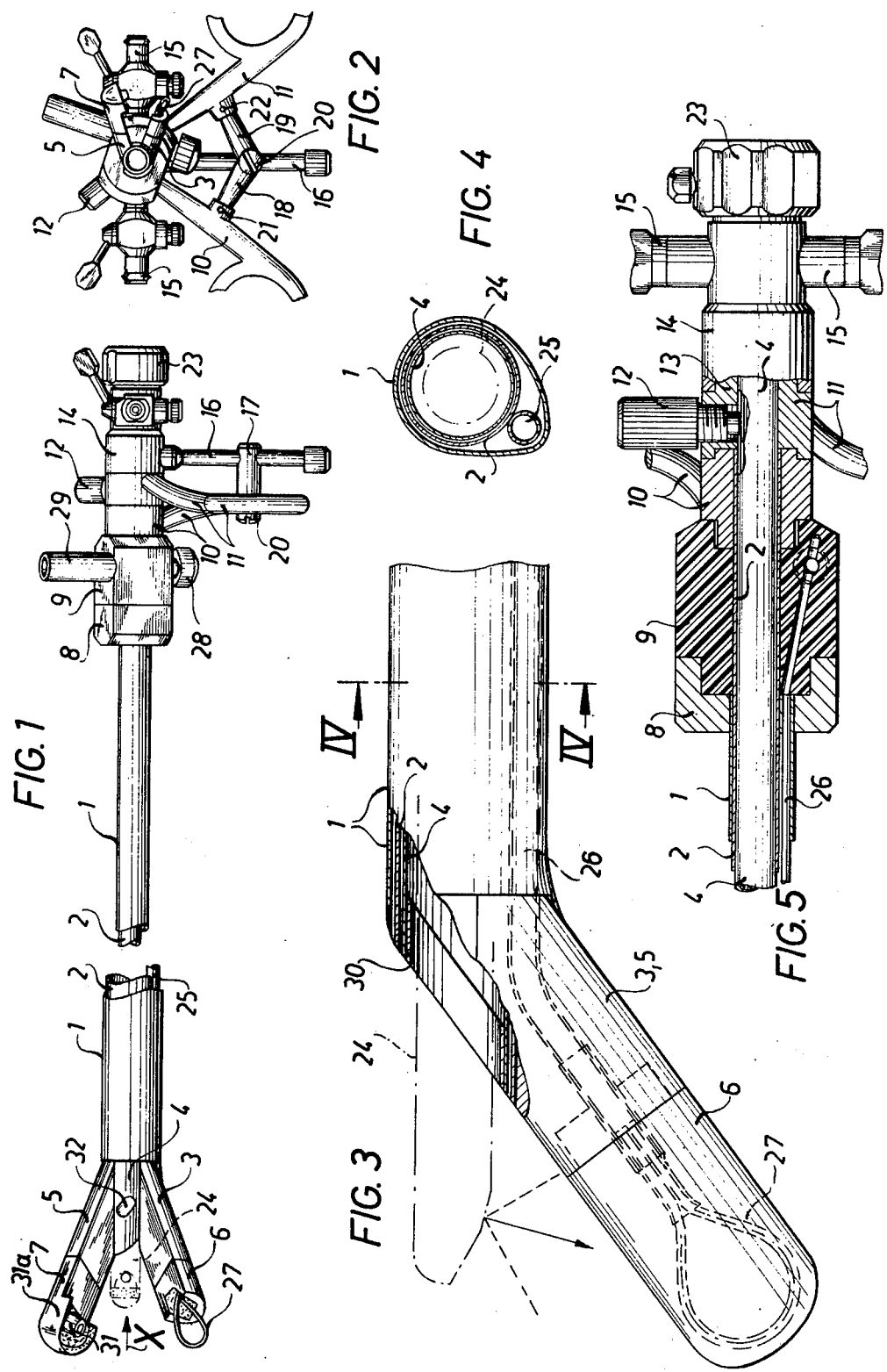

RESECTOSCOPES

BACKGROUND OF THE INVENTION

1. Field of the Invention

This invention relates to resectoscopes.

In this specification the term "resectoscope" includes within its ambit instruments for removing papillomas and tumors of the bladder as well as instruments for transurethral prostatic resection.

2. Description of the Prior Art

To remove enlarged prostates and to cut away papillomas and tumors of the bladder, what have hitherto been used are resectoscopes which, for excision purposes, employ a cutting electrode which is supplied with HF current. The cutting electrode is movable in the longitudinal direction with respect to the straight outer barrel, and, when for example a sprung handle is actuated manually, executes a movement of predetermined size so that the tissue to be removed can be taken away piece by piece while under observation.

While there is no difficulty in removing prostates with existing resectoscopes, it is only with difficulty that tumors and papillomas in the bladder region, and in particular at the sides of the neck of the bladder, can be examined and removed, due to the fact that with known resectoscopes, which in any case are fitted with directly forward-looking optical systems, anatomical conditions will permit only a limited radius of action.

SUMMARY OF THE INVENTION

Accordingly, the main object of the present invention is to provide a resectoscope with which the whole of the bladder region can readily be reached and can be examined with a sideways-looking optical system such as is used for inspecting the bladder, so that excisions can be performed from all parts of the bladder without difficulty.

To this end, the invention consists in a resectoscope comprising an outer barrel which, being secured to an inner guide tube, is connected to one limb of a scissors grip at the proximal end and is angled at the distal end to form a forceps jaw which holds a cutting loop in an insulated state, and an inner tube to hold the optical system which inner tube extends through the guide tube, is connected to the other limb of the scissors grip at the proximal end, and is angled at the distal end to form the second forceps jaw, which cooperates with the cutting loop.

By means of this design, it is now easily possible, due to the angled forceps jaws, to reach and make excisions from the bottom of the bladder lying opposite the urinary tract and the sides of the bladder immediately adjacent its neck, while for excising prostates, known resectoscopes, which are capable of making larger cuts and of removing the prostate more quickly, can still be used.

BRIEF DESCRIPTION OF THE DRAWINGS

FIG. 1 shows a side view of one embodiment of resectoscope according to the invention, with the distal part enlarged and the forceps jaws open, FIG. 2 shows an end-on view of the distal end of the resectoscope, looking in the direction of arrow X of FIG. 1, FIG. 3 shows an enlarged side-view of the distal end of the resectoscope when turned through 90° with respect to FIG. 1, FIG. 4 shows a cross-section on line IV—IV of FIG. 3, FIG. 5 shows the proximal end of the resectoscope, partly in section and partly in elevation, to a larger scale than FIG. 1.

DESCRIPTION OF THE PREFERRED EMBODIMENT

In the embodiment shown, the barrel or outer tube 1 of the resectoscope is of generally ovoid shape or has a cross-section of circular shape with a parabolic bulge at one side (FIG. 4). A guide-tube 2 of circular cross-section is soldered into the outer tube 1. Through the guide-tube 2 extends an inner tube 4. The outer tube 1 is angled at the distal end of the resectoscope to form one jaw 3 of a forceps and the inner tube 4 is angled to form the other jaw 5 and the two jaws 3, 5 extend into insulating parts 6 and 7.

At the proximal end of the resectoscope the outer tube 1 is soldered into a turned part 8, while the guide-tube 2 extends through a further, succeeding insulating part 9 and is then soldered to a part of one limb 10 of the limbs of a scissors grip, which surrounds it. Parts 1, 2, 8, 9 and 10 form a solid, rigid unit.

At the proximal end of the resectoscope the inner tube 4 terminates inside a part of the other limb 11 of the scissors grip which encloses it, and is releasably connected to limb 11 by a locking screw 12. When the locking screw 12 is released, the inner tube 4 can be withdrawn from the distal end and cleaned and disinfected. A shoulder 13 on the part of limb 11 which encloses or encircles the inner tube 4 engages in a final turned part 14 which carries the cocks 15 required for continuous sustained irrigation, which cocks discharge between the inner tube 4 and an optical system 24 passing therethrough. Part 14 is connected to the shoulder 13 by means of a guidescrew 16.

On screw 16 slides a bridge piece 17 which carries a mounting spigot on which two toggle links 18, 19 are mounted to pivot, the links being held in place by a retainer screw 20. These toggle links are also pivotally connected to the limbs 10 and 11 of the scissors grip at 21 and 22. Forming the scissors grip in this way ensures that the forceps jaws 3, 5 will open and close by the same amount. The optical system 24, which is indicated in broken lines, is connected to the outer tube 1 by a turned sealing part 23 which forms the proximal termination of the resectoscope.

The parabolic bulge at one side of the outer tube 1 is used to hold a guide tube 25 for an electrode 26. At the distal end of the resectoscope the electrode 26 extends into a cutting loop 27 in insulator 6 and at the proximal end of the resectoscope the electrode is connected to an HF connection 29 by means of a clamping screw 28.

During excision, the area in which cutting loop 27 operates is thoroughly irrigated, with the irrigating liquid flowing between inner tube 4 and optical system 24 in the distal direction. An annular deflector 30 which is soldered into the inner tube 4 at the distal end, ensures that the irrigating liquid flows out through a longitudinally extending passage in jaw 5, through a hollow, insulated projection 31 and onto the loop 27. In addition, because of the increase in pressure, liquid also flows through a bore 32 provided in the inner tube 4 between jaws 3 and 5 and into the area where excision is taking place, that is to say between parts 6 and 7 of the jaws. The annular deflector 30 increases the pressure of liquid in the resectoscope and because of this the desired flow takes place through the passage in jaw 5 and bore 32. The insulated projection 31 has a particular advantage in that, when jaws 3, 5 are fully closed, it forces any tissue which may have remained clinging to loop 27 out of the loop.

Spaced from and surrounding the insulated projection 31 is a hood-like portion 31a of the insulating part 7. When the jaws are closed, the cutting loop 27 fits around projection 31 inside the rim of hood 31a, which assists in cutting or dividing the tissue. In addition the rim of hood 31a forms a shield when the resectoscope is inserted into the urinary tract with the jaws closed, to cover up the loop 27 so that it cannot damage the tract. Alternatively, the jaws 3 and 5 could form parts of the tubes 4 and 1 respectively.

I claim:
1. A resectoscope comprising:
   a. a barrel,
   b. a guide tube in and secured to said barrel,
   c. said barrel having
      i. an end portion which is at a distal end region of the resectoscope and which is inclined at an angle with respect to the direction of said barrel,
   d. an inner tube for receiving an optical system to be passed therethrough, said inner tube extending through said guide tube,
   e. said inner tube having
      i. an end portion which is at a distal end region of the resectoscope and which is inclined at an angle with respect to the direction of said inner tube,
   f. forceps comprising
      i. two jaws which are constituted respectively by the angled end portions of said barrel and inner tube, and
      ii. a scissors grip comprising two limbs which are connected respectively to said barrel and inner tube at a proximal end region of the resectoscope,
   g. a conductive cutting loop carried by one of said jaws to be co-operated with by the other of said jaws, and
   h. electrical connection means for said cutting loop.

2. A resectoscope according to claim 1, wherein the other of said jaws has a terminal insulating part provided with a projection positioned to pass through said cutting loop upon jaw closure.

3. A resectoscope according to claim 2, wherein the insulating part of said other jaw includes a hood having a rim and which is spaced from said projection, whereby when the jaws are closed said cutting loop extends around said projection inside the rim of the hood.

4. A resectoscope according to claim 1, and comprising an optical system extending through said inner tube and defining therewith a first passage for receiving an irrigation liquid, at least one irrigation cock communicating with said passage, said inner tube having a wall portion defining a bore in communication with said first passage and opening between said jaws, said other jaw defining a second passage in communication with said first passage and having a hollow projection positioned to pass through said cutting loop upon jaw closure and in communication with said second passage, and an annular deflector secured to a distal end region of said inner tube positioned for deflecting irrigation liquid flowing from the first passage through said bore in the inner tube wall portion and through said second passage in said other jaw and through said hollow projection to said cutting loop.

5. A resectoscope according to claim 4, wherein said cutting loop and hollow projection are carried respectively by the jaws which are constituted by the angled end portions of said barrel and said inner tube, said jaws having terminal insulating parts which insulate said cutting loop and carry said hollow projection respectively, a turned part at the proximal end region of the resectoscope and to which said barrel is secured, an insulator receiving said guide tube and being secured to one of the limbs of said scissors grip, said inner tube terminating inside the other limb of said scissors grip and being releasably connected to said other limb, two irrigation cocks supported outward of said inner tube and being in communication with said first passage, said electrical connection means including a high frequency connection carried by said insulator and means including a clamping screw on said insulator connecting said cutting loop to said high frequency connection.

6. A resectoscope according to claim 1, wherein the barrel, in cross-section, has a parabolic bulge defining with said guide tube a space, a further guide tube extending through said space said electrical connection means for said cutting loop being extended through said further guide tube.

7. A resectoscope according to claim 1, including means for releasably connecting said inner tube to one of said limbs of said scissors grip.

* * * * *